US00PP24811P3

(12) United States Plant Patent
Weber

(10) Patent No.: US PP24,811 P3
(45) Date of Patent: Aug. 26, 2014

(54) RASPBERRY PLANT NAMED 'DOUBLE GOLD'

(50) Latin Name: ***Rubus idaeus* L.**
Varietal Denomination: Double Gold

(71) Applicant: Cornell University, Ithaca, NY (US)

(72) Inventor: Courtney A. Weber, Geneva, NY (US)

(73) Assignee: Cornell University, Ithaca, NY (US)

( * ) Notice: Subject to any disclaimer, the term of this patent is extended or adjusted under 35 U.S.C. 154(b) by 80 days.

(21) Appl. No.: 13/694,084

(22) Filed: Oct. 30, 2012

(65) Prior Publication Data

US 2014/0123349 P1 May 1, 2014

(51) Int. Cl.
*A01H 5/00* (2006.01)

(52) U.S. Cl.
USPC ..... Plt./204

(58) Field of Classification Search
USPC ..... Plt./204
See application file for complete search history.

(56) References Cited

PUBLICATIONS

"Berry Different: Growers Turn To New Cornell Raspberries For Better Flavor, Disease-Resistance And A Colorful Fall Crop," Dec. 7, 2012, Retrieved from the web on Feb. 10, 2013, <http://www.blogs.cornell.edu/stationnews/2012/12/07/berry-different-growers-turn-to-new-cornell-raspberries-for -better-flavor-disease-resistance-and a -colorful-fall-crop/>, pp. 1-2.
"'Double Gold' Raspberries," Retrieved from web on Feb. 10, 2013, <http://www.cctec.cornell.edu/events/celebration12/Double%20Gold.pdf>, p. 1.
Frazer, K., "Growers License New Raspberries," Retrieved from web on Feb. 10, 2013, <blogs.cornell.edu/fruit/2012/12/05/growers-license-new-raspberries/, pp. 1-2.
Garris, A. "Cornell Releases Two New Raspberry Varieties," Cornell ChronicleOnline, Apr. 30, 2012, Retrieved from web on Feb. 10, 2013, <http://www.news.cornell.edu/stories/April12/Raspberries.html>, pp. 1-2.
Garris, A. "Cornell Releases Two New Raspberry Varieties," Cornell Chronicle, May 4, 2012, p. 1, vol. 43, No. 33.
"Golden Raspberry 'Double Gold,'" Retrieved from web on Feb. 10, 2013, <http://www.cornell.flintbox.com/public/project/21194>, pp. 1-2.
"Nursery Guide for Berry & Small Fruit Crops," Retrieved from web on Feb. 10, 2013, <http://www.fruit.cornell.edu/berry/nurseries/raspberries.html>, pp. 1-3.

*Primary Examiner* — Annette Para
(74) *Attorney, Agent, or Firm* — MacMillan, Sobanski & Todd, LLC

(57) ABSTRACT

This invention relates to a new and distinct everbearing raspberry plant designated as 'Double Gold' primarily adapted to growing conditions of west central New York and other regions of similar climate. The new plant is primarily characterized by golden to orange/red conical fruit that is equally long and broad, vigorous tall canes, late season primocane production and early mid-season floricane production.

5 Drawing Sheets

Genus and species: *Rubus idaeus* L.
Variety denomination: 'Double Gold'.

BACKGROUND AND SUMMARY OF THE INVENTION

I. Field & Utility Summary

This invention relates to a new and distinct everbearing raspberry plant designated as 'Double Gold' primarily adapted to growing conditions of west central New York and other regions of similar climate. The new plant is primarily characterized by golden to orange/red conical fruit that is equally long and broad, vigorous tall canes, late season primocane production and early mid-season floricane production.

Raspberry plant 'Double Gold' is primarily adapted to the climate and growing conditions of west central New York and other regions of similar temperate climate. This climate allows for the development of very tall primocanes that produce fruit in the late fall season from late September to early November. 'Double Gold' benefits from the use of protective structures such as plastic hoop houses or high tunnels, which allow for optimal cane growth and the complete harvest of the fall crop when the risk of frost is prevalent. The long canes make harvest of a floricane crop on the same canes the following year from late June through late July feasible.

II. Cultivation Summary

The new and distinct red raspberry originated from a hand-pollinated cross of the maternal parent Cornell NY319 (unpatented) with paternal parent 'Graton Gold' (U.S. Plant Pat. No. 7,625).

III. Comparisons

The following traits have been repeatedly observed and are determined to be unique characteristics of 'Double Gold', which in combination distinguish this raspberry plant as a new and distinct plant:

1. late fall fruit harvest on primocanes;
2. early mid-summer harvest on floricanes;
3. very tall canes;
4. high vigor with heavy cane production;
5. golden to orange/red, glossy conical fruit.

'Double Gold' has amber fruit when developing and orange/red, conical fruit when fully ripe. 'Double Gold' fruits both on late fall primocane and early/mid floricane. The canes of 'Double Gold' are very tall, have 3-foliate leaves, are extensively pigmented red/purple, lack an obvious waxy coating, and have a moderate number of short, stout spines.

Maternal parent plant NY319 bears large red conical fruit on shorter primocanes that are less vigorous and tall than 'Double Gold'.

Paternal parent plant 'Graton Gold' (U.S. Plant Pat. No. 7,625) bears small round golden/orange fruit (2.2 g) on green primocanes with 5-foliate leaves. 'Graton Gold' is a moderately late fall fruiting plant.

Unrelated plant 'Crimson Giant' (U.S. Plant Pat. No. 23,375) bears red fruit and has canes that are less pigmented than 'Double Gold'.

Unrelated plant 'Prelude' (U.S. Plant Pat. No. 11,747) bears round red fruit on greyed-orange canes. 'Prelude' produces fruit on an average of 11 primocane laterals and 17 floricane laterals.

Unrelated plant 'Caroline' (U.S. Plant Pat. No. 10,412) bears red conical fruit on red/purple and greyed-yellow canes. 'Prelude' produces fruit on an average of 14 primocane laterals and 10 floricane laterals.

'Caroline', 'Prelude' and 'Double Gold' differ by the following combination of characteristics described in Table 1. Color terminology is based on The Royal Horticultural Society colour chart (2001 edition).

TABLE 1

| Characteristic | 'Double Gold' | 'Caroline' (PP10,412) | 'Prelude' (PP11,747) |
|---|---|---|---|
| 1. Mature primocane color | Red purple 63B to 63C | Red purple 59B Greyed-yellow 160A. | Greyed-orange164A |
| 2. Fruit shape | Broad conical | Broad conical | Round |
| 3. Fruit length (mm) | 19.3 | 18 | 15 |
| 4. Fruit width (mm) | 18.6 | 19 | 17.5 |
| 5. Fruit length × width ratio | 1.04 | 0.95 | 0.86 |
| 6. Mean fruit weight | 2.65 g | 2.5 g | 2.2 |
| 7. Maximum fruit weight | 3.5 | 3.8 | 3.5 |
| 8. Mature fruit color | Orange red 33A | Red 45A | Red 39A |
| 9. Canes per plant | 21 | 21 | 11 |
| 10. Fruiting laterals per primocane | 13 | 14 | 11 |
| 11. Fruiting laterals per floricane | 30 | 10 | 17 |
| 12. Leaflet number | 3 | 5 | 3 |

IV. Breeding History

The new and distinct red raspberry originated from a hand-pollinated cross of the Cornell NY319 (maternal—Unpatented)×'Graton Gold' (paternal—U.S. Plant Pat. No. 7,625). This cross was made and the resulting seedling grown in Geneva, N.Y. The seedling was selected from a controlled breeding plot in 2004 and was designated NY04-25 for testing. NY04-25 was subsequently designated 'Double Gold'.

V. Asexual Reproduction

Raspberry plant 'Double Gold' has been asexually propagated by dormant canes in Geneva, N.Y. since 2005 and was established in tissue culture in Geneva, N.Y. in 2008.

VI. Stability

Asexual propagation as described has demonstrated that the combination of traits that characterize this plant are fixed and remain true to type through successive generations.

BRIEF DESCRIPTION OF THE FIGURES

The accompanying color photographs show typical specimens of the new plant at various stages of development as nearly true as it is possible to make in color reproductions. Color in the photographs may differ slightly from the color value cited in the detailed botanical description, which accurately describes the color of 'Double Gold'. The photographs of canes and fruit were taken in Geneva, N.Y. in the second year of harvesting fruit.

DETAILED BOTANICAL DESCRIPTION OF THE INVENTION

Figure 1:
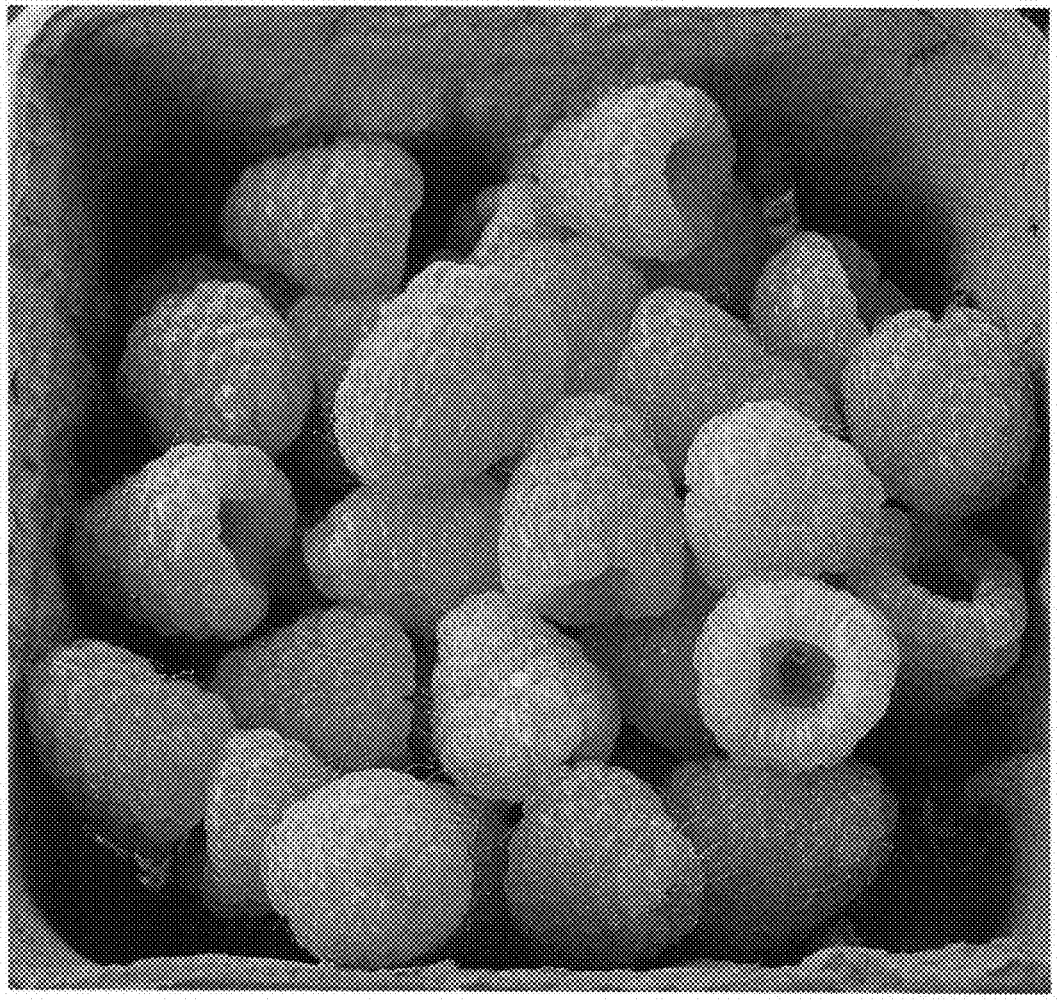
FIG. 1 Typical fruit shape and size of 'Double Gold' in a container
Figure 2:
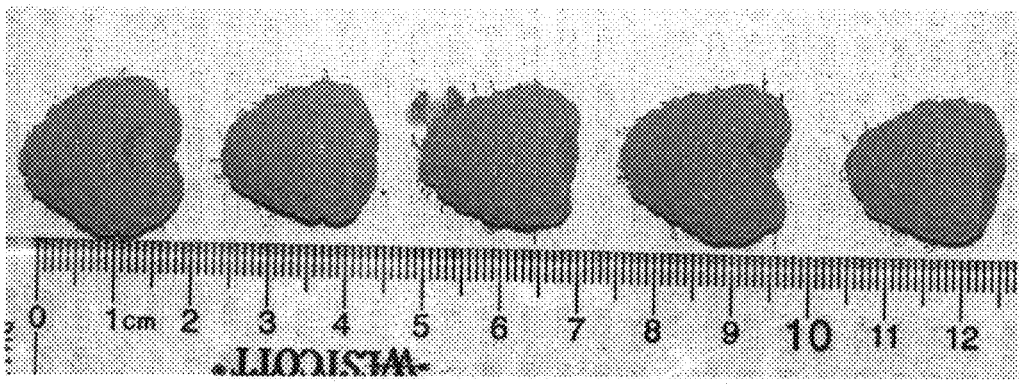
FIG. 2 Typical 'Double Gold' fruit from a side view with increased pigmentation with maturity from left to right FIG. 3A Typical fruit shape of 'Double Gold' and FIG. 3B typical shape of 'Polka' for comparison FIG. 4A Typical primocane pigmentation viewed from two sides of the same cane for 'Double Gold' and FIG. 4B for 'Caroline'
Figure 3A:
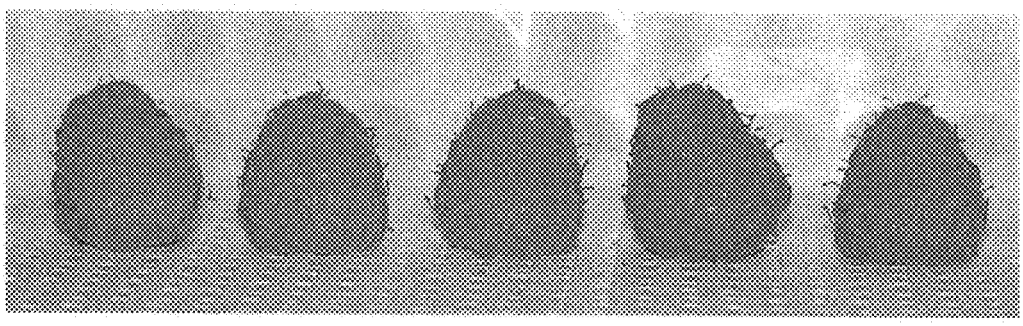
Figure 3B:
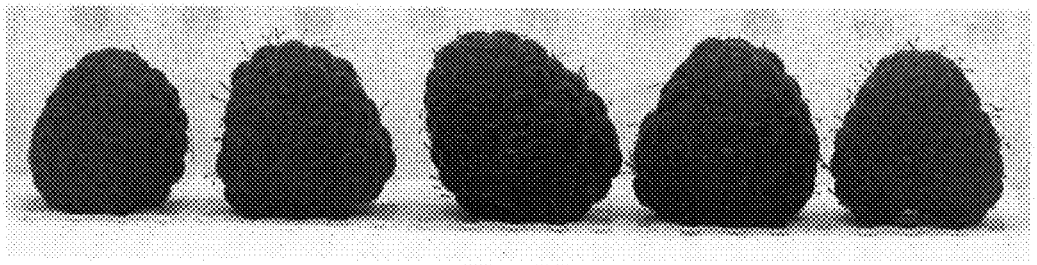
Figure 4A:
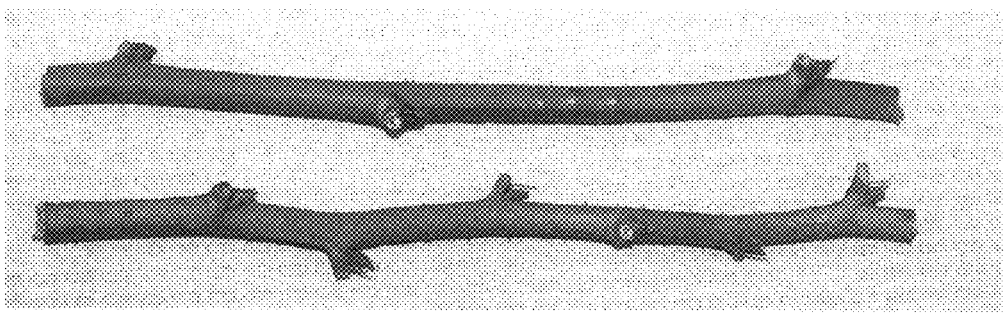
Figure 4B:
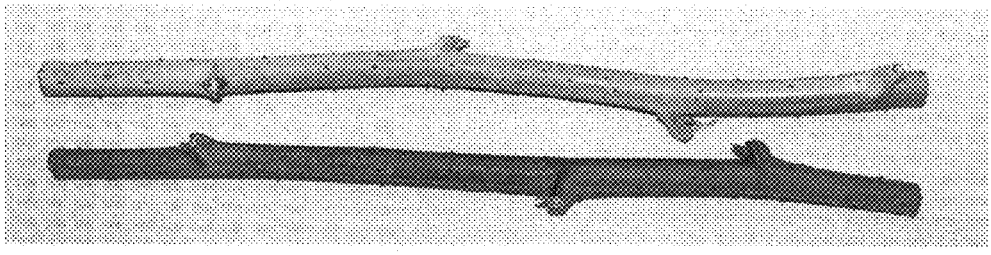
Figure 5A:
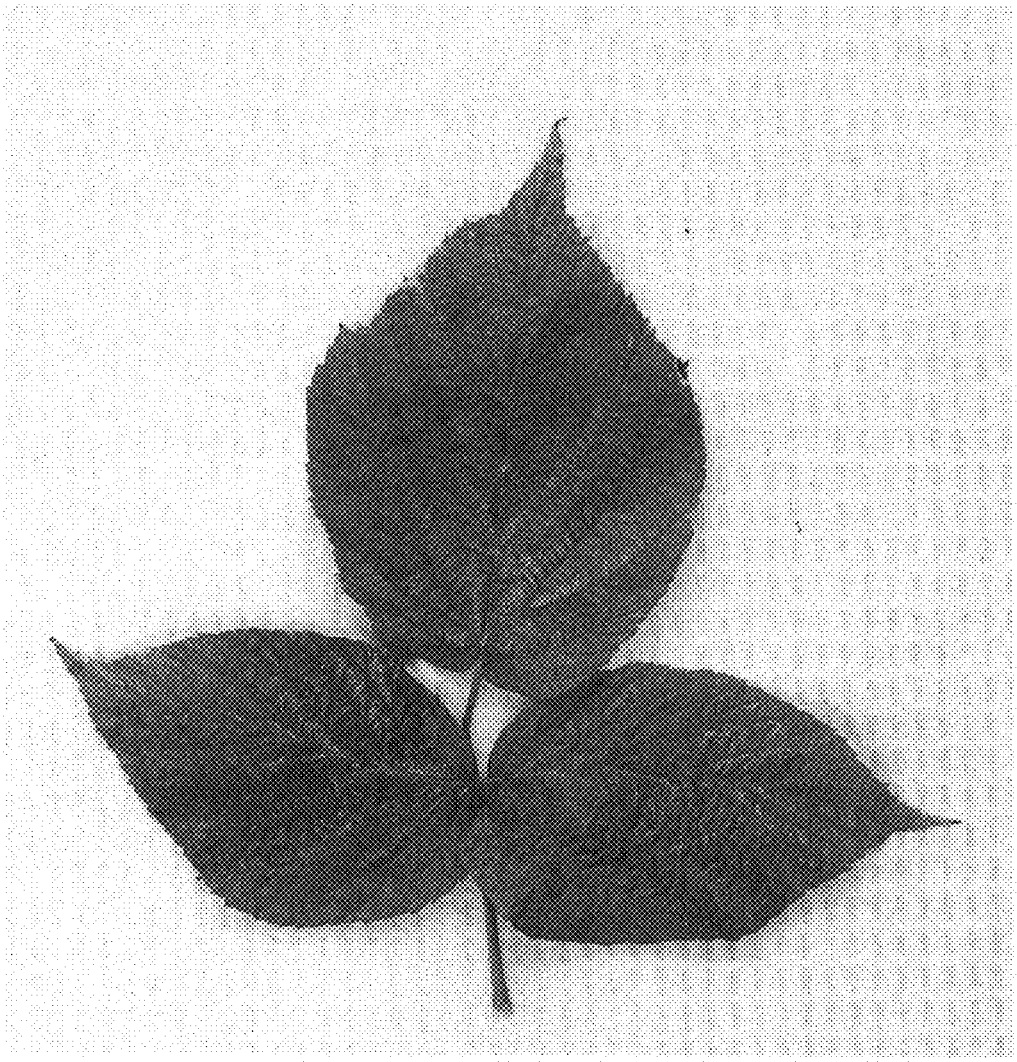
FIG. 5A Mature leaves nearing senescence showing pigmentation and leaflet number for 'Double Gold' and FIG. 5B for 'Caroline'
Figure 5B:
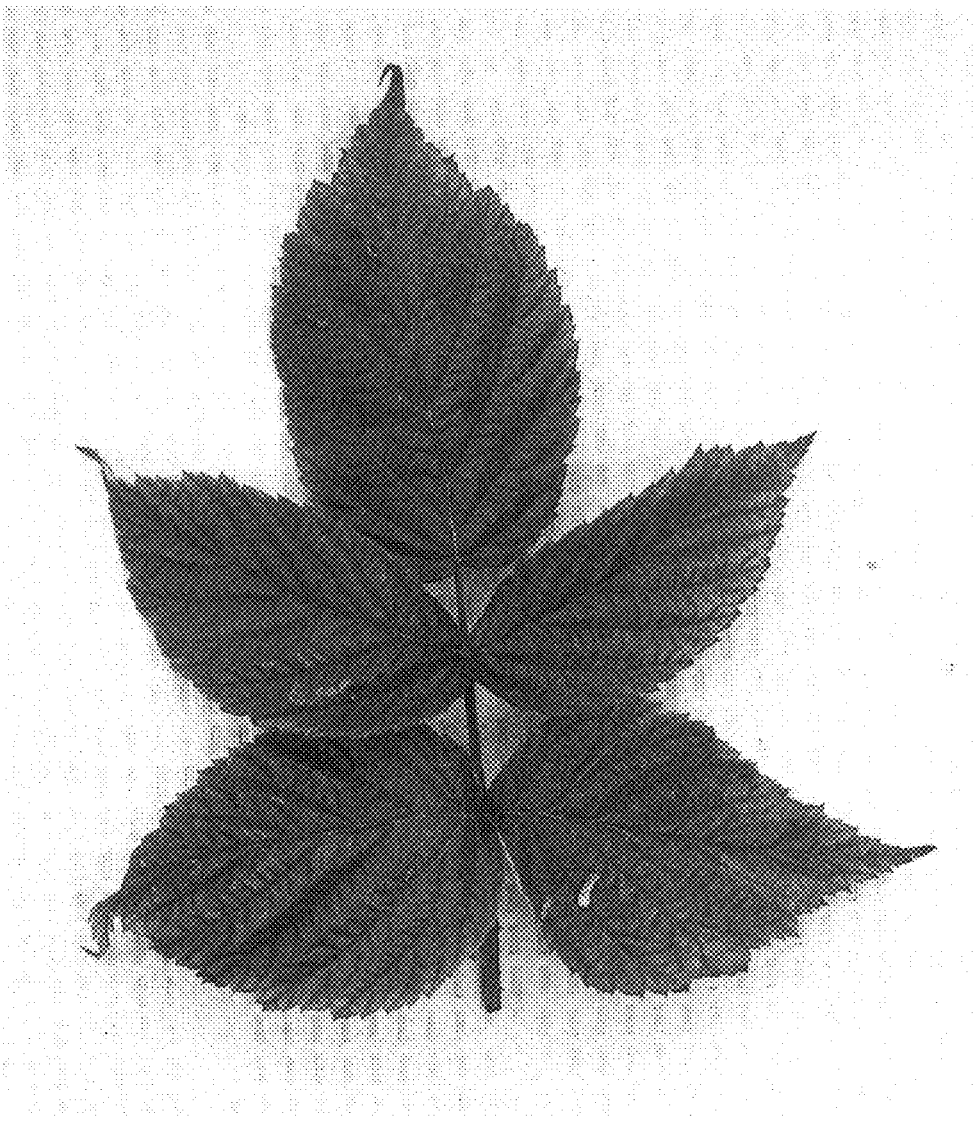

'Double Gold' has not been observed under all possible environmental conditions and as such the characteristics may vary in detail depending on weather conditions, day length, soil type and location.

The photographs together with the description of the new raspberry 'Double Gold' are based upon the observations taken during the 2012 growing season in Geneva, N.Y. Measurements were taken on plants grown in a perennial planting in a high tunnel system that was planted in Geneva, N.Y. in 2009 with the canes emerging naturally in April 2012. Flower measurements and characteristics were taken from secondary flowers and fruit measurements from secondary fruit. Mean measurements of fruit size were taken on 10 fruit samples throughout the season. Measurements of flower and fruit parts are means of 10 fruit samples. Cane measurements taken within the center third of the cane unless otherwise noted.

Primocanes:

*Cane color.*—Red purple 63B to 63C.

*Spines.*—Present.

*Cane length.*—2.0 m-2.3 m; mean 2.15 m.

*Cane diameter.*—7-11 mm; mean 9 mm.

*Number of primocane fruiting lateral branches.*—11-14; mean 13.

*Maximum primocane fruiting lateral length.*—12 cm.

*Number of floricane fruiting lateral branches.*—31-35; mean 33.

*Maximum floricane fruiting lateral length.*—42 cm.

*Pubescence.*—None.

Spines:

*Density.*—High at base, moderate at middle third.

*Form.*—Stout.

*Length.*—Mean 1.5 mm.

*Apex.*—Curved downward slightly.

*Color.*—Red purple 63B.

Leaves:

*Type.*—Compound; typically 3 leaflets.

*Mature leaflet color.*—Upper surface Green 143AA; lower surface Green 138D.

*Arrangement.*—Free.

*Terminal leaflet length.*—8.9-12.6 cm; mean 10.5 cm.

*Terminal leaflet width.*—5.0-9.6 cm; mean 6.6 cm.

*Terminal leaflet length to width ratio.*—1.6.

*Basal leaflet length.*—6.5-10.4 cm; mean 8.2 cm.

*Basal leaflet width.*—3.6-5.3 cm; mean 4.4 cm.
*Basal leaflet length to width ratio.*—1.8.
*Leaflet shape.*—Ovate.
*Terminal leaflet tip.*—Cuspidate.
*Basal leaflet tip.*—Auriculate.
*Leaflet margins.*—Doubly serrate.
*Terminal leaflet number of serrations.*—Mean 89.
*Basal leaf attachment.*—Flush.
*Leaflet overlap.*—Little to none.
*Petiole length.*—4.4 cm.
*Petiole width.*—2-3 mm.
*Petiole spines.*—Present.
*Petiole spine apex.*—Slight curve toward stem.
*Petiole color.*—Red purple 63B.

Stipules:
*Quantity per leaf.*—2.
*Shape.*—Straight and erect.
*Length.*—5-7 mm; mean 5.6 mm.
*Color.*—Red purple 63B.

Flowers:
*Diameter.*—1.6-2.1 cm; mean 1.8 cm.
*Bud shape.*—Conical.
*Fragrance.*—None.
*Petals number.*—Typically 5; occasionally 6 or 7.
*Petal shape.*—Lanceolate.
*Petal length.*—7-8 mm; mean 7.6 mm.
*Petal width.*—2.5-3 mm; mean 2.9 mm.
*Petal length to width ratio.*—2.9.
*Petal color.*—White 155C.
*Sepal number.*—5 or 6 typically, occasionally 7; mean 5.7.
*Sepal length.*—7-8 mm; mean 7.5 mm.
*Sepal color.*—Yellow-green N144D.
*Mean stigma number.*—110.
*Stigma color.*—White 155B.
*Mean stamen number.*—65.
*Anther color.*—White 155A.
*Anther filament color.*—White 155D.
*Stamen height.*—Above to equal stigmatic surface.

Fruit:
*Shape.*—Broad conic.
*Fruit length.*—1.8-2.1 cm; mean 1.9 cm.
*Fruit width.*—1.6-2.0 cm; mean 1.9 cm.
*Fruit length to width ratio.*—1.0.
*Weight.*—1.8-3.5 g; mean 2.65 g.
*Number of drupelets.*—65.
*Color of mature fruit.*—Orange N25A early to orange-red 33A at full maturity.
*Pedicel diameter.*—1 mm.
*Pedicel spines.*—Present; curved back towards cane.
*Adherence to receptacle.*—Moderate.

I claim:

1. A new and distinct raspberry plant as herein described and illustrated.

* * * * *